US008562591B2

(12) United States Patent
Ali et al.

(10) Patent No.: US 8,562,591 B2
(45) Date of Patent: *Oct. 22, 2013

(54) DRUG INFUSION SYSTEM AND METHOD ADAPTED TO START DURING PROGRAMMING CYCLE

(75) Inventors: Irfan Z. Ali, Woodbury, MN (US); David C. Ullestad, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,945

(22) Filed: Jul. 18, 2012

(65) Prior Publication Data

US 2012/0283704 A1    Nov. 8, 2012

Related U.S. Application Data

(60) Division of application No. 10/837,500, filed on Apr. 30, 2004, now Pat. No. 8,241,270, which is a continuation-in-part of application No. 10/459,672, filed on Jun. 11, 2003, now Pat. No. 7,008,413, which is a division of application No. 09/302,613, filed on Apr. 30, 1999, now Pat. No. 6,579,280.

(60) Provisional application No. 60/508,019, filed on Oct. 2, 2003, provisional application No. 60/496,968, filed on Aug. 20, 2003.

(51) Int. Cl.
*A61K 9/22* (2006.01)
*A61M 31/00* (2006.01)

(52) U.S. Cl.
USPC ........................ 604/891.1; 604/502

(58) Field of Classification Search
USPC ............ 604/67, 890.1, 891.1, 131, 151, 502; 700/281–282; 239/69; 222/14, 638; 340/309.4, 309.7, 309.16
See application file for complete search history.

(56) References Cited

U.S. PATENT DOCUMENTS

| | | | | |
|---|---|---|---|---|
| 4,146,029 A * | 3/1979 | Ellinwood, Jr. | ............ | 604/891.1 |
| 4,504,153 A * | 3/1985 | Schollmeyer et al. | ........... | 368/10 |
| 4,731,051 A * | 3/1988 | Fischell | .......................... | 604/67 |
| 6,416,493 B1 * | 7/2002 | Del Giglio | ................. | 604/96.01 |
| 6,579,280 B1 * | 6/2003 | Kovach et al. | ............. | 604/891.1 |
| 7,008,413 B2 * | 3/2006 | Kovach et al. | ............. | 604/891.1 |
| 8,241,270 B2 * | 8/2012 | Ali et al. | ..................... | 604/891.1 |
| 2002/0193679 A1 * | 12/2002 | Malave et al. | ................ | 600/407 |
| 2003/0036783 A1 * | 2/2003 | Bauhahn et al. | ................ | 607/59 |
| 2004/0077997 A1 * | 4/2004 | Jasperson et al. | ............... | 604/67 |

* cited by examiner

*Primary Examiner* — Kevin C. Sirmons
*Assistant Examiner* — Andrew Gilbert
(74) *Attorney, Agent, or Firm* — IPLM Group, P.A.

(57) ABSTRACT

Drug infusion system capable of delivering a fluid medication to a patient and method for doing same is described. An implantable drug delivery device is capable of delivering the fluid medication at a programmable rate to the patient under control of an original programming cycle having a plurality of steps in a plurality of time slots beginning at a starting time. The programming cycle specifies the programmable rate for each of the plurality of steps. An external controller is capable of storing a program representative of the original programming cycle in the implantable drug delivery device at a programming time. The drug infusion system adjusts the implantable drug delivery device so that the original programming cycle will begin at a time during the original programming cycle adjusted for the programming time.

16 Claims, 9 Drawing Sheets

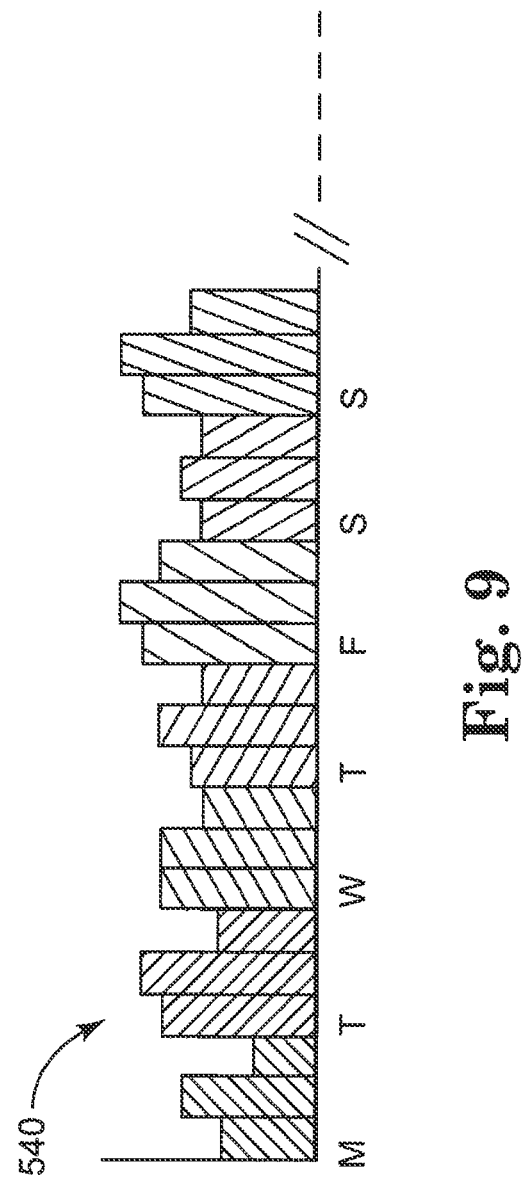

DRUG INFUSION SYSTEM AND METHOD ADAPTED TO START DURING PROGRAMMING CYCLE

RELATED APPLICATIONS

This application is a divisional of U.S. patent application Ser. No. 10/837,500, filed Apr. 30, 2004, now U.S. Pat. No. 8,241,270, issued Aug. 14, 2012, entitled "Drug Infusion System and Method Adapted to Start During Programming Cycle"; which was a continuation-in-part of U.S. patent application Ser. No. 10/459,672, filed Jun. 11, 2003, now U.S. Pat. No. 7,008,413, issued Mar. 7, 2006, entitled "Generic Multi-Step Therapeutic Treatment Protocol"; which was a divisional of U.S. patent application Ser. No. 09/302,613, filed Apr. 30, 1999, now U.S. Pat. No. 6,579,280, issued Jun. 17, 2003 entitled "Generic Multi-Step Therapeutic Treatment Protocol", all of which applications are incorporated herein by reference in their entireties.

This application also claims the benefit of U.S. Provisional Patent Application No. 60/508,019, filed Oct. 2, 2003, entitled "Method and Apparatus for Multi-Step Prescription Table Display and Download in Implantable Pump"; and U.S. Provisional Patent Application No. 60/496,968, filed Aug. 20, 2003, entitled "Method and Apparatus for Multi-Step Prescription Table Display and Download in Implantable Pump", both of which applications are incorporated herein by reference in their entireties.

FIELD OF THE INVENTION

This invention relates to drug infusion systems and, in particular, drug infusion systems that are programmable.

BACKGROUND OF THE INVENTION

Drug infusion systems dispense fluid medication, containing a drug, to a patient. Some drug infusion systems are portable, allowing a patient to receive fluid medication while remaining mobile. In addition, some drug infusion systems are implantable to more effectively and less obtrusively dispense such fluid medication to a patient.

Implantable devices and techniques for treating a patient by drug infusion are well known in the prior art. For instance, U.S. Pat. No. 5,782,798, Rise, entitled "Techniques For Treating Eating Disorders By Brain Stimulation and Drug Infusion"; and U.S. Pat. No. 5,814,014, Eisberry et al, "Techniques of Treating Neurodegenerative Disorders by Brain Infusion", each assigned to Medtronic, Inc., Minneapolis, Minn., disclose such devices and techniques and are hereby incorporated by reference.

Another example of a drug infusion device is shown in U.S. Pat. No. 3,527,220, Summers, entitled "Implantable Drug Administrator", an implantable drug administrator having a refillable bladder which can be filled with a drug and a pump for selectively pumping the drug from the bladder into any desired area of the body. The administrator includes an indicator for indicating when the desired amount of the drug has been injected.

In U.S. Pat. No. 3,951,147, Tucker et al, entitled "Implantable Infusate Pump", a rechargeable infusate pump for implantation in the human body can be refilled periodically by injection through an inlet septum under the skin. A conduit conducts fluid to an infusion site in the body. The pump outlet includes a special controller flow controller which is able to very accurately meter the infusate to the selected body site.

U.S. Pat. No. 4,692,147, Duggan, "Drug Administration Device", assigned to Medtronic, Inc., Minneapolis, Minn., discloses an implantable drug administration device which can be non-invasively programmed to change both the dosage amount and the dosage interval. Verification of the received dosage and interval commands is achieved by means of an audio transducer which is attached to the device case.

The implantable drug administration device described in Duggan allows a medical professional to program to the delivery rate of a drug contained in the reservoir of the device over a specified interval. The process, however, to achieve an even reasonably complex dosing regimen is laborious and time consuming. Each interval must be specified and the particular delivery rate must be individually programmed. For all but the simplest of dosing regimens, this system is not only laborious and takes too long to program but also prone to error due to the painstaking programming steps which must be accomplished.

Implantable drug infusion devices and systems are commonly programmable with a plurality of programming steps. Each programming step typically is conducted for a specific time or a specific period of time and specifies an amount of fluid medication or a rate of delivery of fluid medication to a patient. A plurality of programming steps can typically be sequenced to create a programming cycle delivering fluid medication to a patient at different rates on different days and, perhaps, at different times.

A program cycle is typically designed, i.e., planned and developed, to cover a set of known time periods, e.g., a period of one week. Each day of the week could be separately programmed or one program could during each week day and a different program could run on a weekend day, for example. Each step in the program cycle, perhaps each hour of the day, could have a different programmed delivery amount or delivery rate.

As an example, drug infusion devices could deliver more pain medication during night-time hours when a patient has a need to sleep and less pain medication during waking hours. Other patient activity schedules can and are accommodated, of course.

Since the program cycle is typically designed to be effective based upon a patient's changing needs during the period of time covered by the programming cycle, the programming cycle typically is essentially constructed with a beginning time corresponding to a natural beginning of the patient's activity cycle. For example, a programming cycle may begin at midnight on Sunday night/Monday morning or perhaps at a time corresponding to the patient's arising at the beginning of the work week, e.g., around 6:00 a.m. to 8:00 a.m. on Monday morning.

Upon implantation of the drug infusion device, the device may need to be programmed, i.e., a new or modified programming cycle may need to be installed, loaded and/or activated. Or, not infrequently, the drug infusion device may need to be adjusted or readjusted to take into account variations in the patient's condition and/or the patient's activities, for example.

Usually the time at which such implantation and/or adjustment or other programming activities occur when convenient for both the medical professional and the patient to schedule a visit. Such a visit usually occurs during daytime hours of a week day, i.e., usually clearly not at a time associated with a natural beginning of a patient's activity cycle.

When initially programmed and/or adjusted, it is usually desirable for the programming cycle to take effect immediately or at a time earlier than the next beginning of the full programming cycle. For example, if a programming cycle ran for a full week with a starting time of 12:01 a.m. on Monday morning and the initial programming and/or adjustment appointment occurred at 3:00 p.m. on Tuesday afternoon, the patient would have to wait until the next Monday morning to take advantage of the new or newly adjusted programming cycle.

Further, a similar but somewhat opposite problem occurs when a medical professional wishes to view or review the programming cycle settings of an existing drug infusion device already being used by a patient. In order to make the drug infusion device as small as possible and to maximize battery life, the programming information is often cryptically installed and formatted in the device. A medical professional who reviews a programming cycle and may wish to modify the programming cycle at 2:00 p.m. on Wednesday afternoon (during an office visit by the patient) may find it cumbersome to be reviewing the middle of a programming cycle.

BRIEF SUMMARY OF THE INVENTION

The present provides a solution to the above-noted problems and provides a mechanism for an easily understood format for a medical professional to view, modify, install, update and/or initiate a programming cycle of a drug infusion device.

The present invention provides a drug infusion system capable of delivering a fluid medication to a patient. An implantable drug delivery device is capable of delivering the fluid medication at a programmable rate to the patient under control of an original programming cycle having a plurality of steps in a plurality of time slots beginning at a starting time. The programming cycle specifies the programmable rate for each of the plurality of steps. An external controller is capable of storing a program representative of the original programming cycle in the implantable drug delivery device at a programming time. The drug infusion system adjusts the implantable drug delivery device so that the original programming cycle will begin at a time during the original programming cycle adjusted for the programming time.

In a preferred embodiment, the adjusting occurs before the program representative of the original programming cycle is stored in the implantable drug delivery device.

In a preferred embodiment, the apparatus further has an adjusted programming cycle having a new start time corresponding to the programming time and wherein the program representative of the original programming cycle comprises the adjusted programming cycle. In a preferred embodiment, the original programming cycle is retained.

In a preferred embodiment, the external controller retains the original programming cycle.

In a preferred embodiment, the implantable drug delivery device retains the original programming cycle.

In a preferred embodiment, the adjusting occurs after the program representative of the original programming cycle is stored in the implantable drug delivery device.

In a preferred embodiment, the start time is adjusted using an offset from the start time to account for the programming time.

In a preferred embodiment, the offset equals an amount of time between the start time and the programming time.

In a preferred embodiment, the offset is stored in the implantable drug delivery device.

In a preferred embodiment, the start time is adjusted using a time obtained from a real time clock to account for the programming time.

In another embodiment, the present invention provides a method of programming an implantable drug delivery device which is adapted to deliver a fluid medication at a programmable rate to a patient in plurality of steps in a plurality of time slots. An original programming cycle is created specifying the programmable rate for each of the plurality of steps on an external controller specifying a starting time for the original programming cycle. A program representative of the original programming cycle is stored in the implantable drug delivery device at a programming time. The implantable drug delivery device is adjusted so that delivery of the fluid medication to the patient will begin at a time during the original programming cycle adjusted for the programming time.

In a preferred embodiment, the starting time and the programming time are different. In a preferred embodiment, the original programming cycle is reconstructable from the adjusted programming cycle.

In a preferred embodiment, the adjusted programming cycle contains flags allowing the original programming cycle to be reconstructed from the adjusted programming cycle.

In a preferred embodiment, the offset equals an amount of time between the start time and a current time obtained from the real time clock.

In a preferred embodiment, the real time clock is external to the implantable drug delivery device.

In a preferred embodiment, the real time clock is internal to the implantable drug delivery device.

In a preferred embodiment, the adjusting step occurs before the storing step.

In a preferred embodiment, the adjusting step comprises the step of creating an adjusted programming cycle having a new start time corresponding to the programming time and wherein the storing step comprises storing the adjusted programming cycle in the implantable drug delivery device.

In a preferred embodiment, a further step retains the original programming cycle.

In a preferred embodiment, the retaining step retains the original programming cycle external to the implantable drug delivery device.

In a preferred embodiment, the retaining step retains the original programming cycle in the implantable drug delivery device.

In a preferred embodiment, the adjusting step occurs after the storing step. In a preferred embodiment, the adjusting step provides an offset from the start time to account for the programming time.

In a preferred embodiment, additionally the offset is stored in the implantable drug delivery device.

In a preferred embodiment, the adjusting step comprises providing an offset from the start time using a time obtained from a real time clock.

BRIEF DESCRIPTION OF THE DRAWINGS

FIG. 9 illustrates a multi-step prescription table with two cycles which are subset of other, having a daily cycle with intra day step changes and then a weekly cycle in which each day of the week may have a different day cycle.

DETAILED DESCRIPTION OF THE INVENTION

The contents of U.S. Pat. No. 4,692,147, Duggan, entitled "Drug Administration Device", is hereby incorporated by reference.

Figure 1:
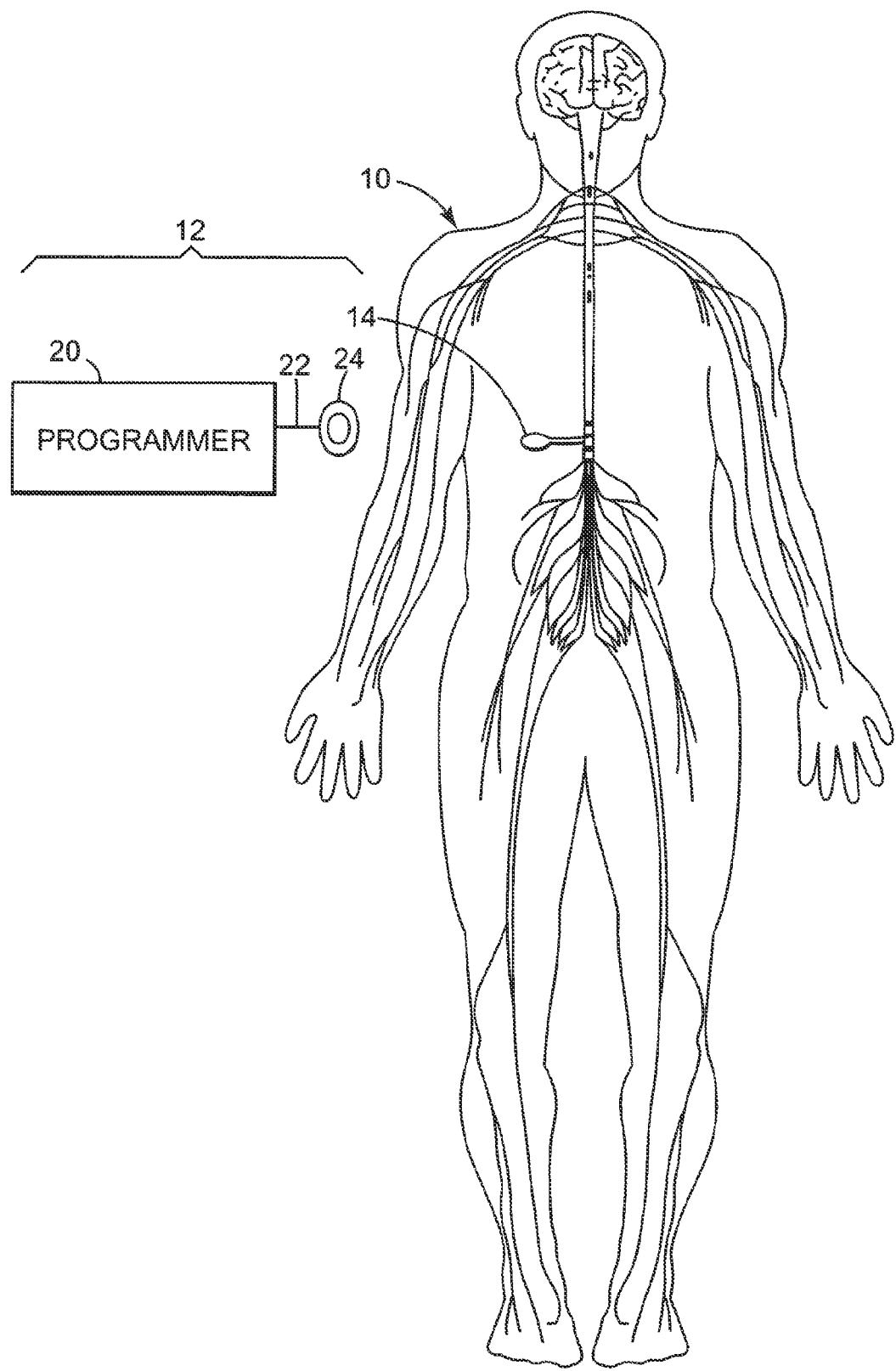
FIG. 1 is a schematic view of a drug infusion system of the present invention having a drug infusion device implanted within the patient's body.

FIG. 1 is a schematic view of drug infusion system 12 of the present invention. Implantable drug infusion device 14 is shown implanted within the body of patient 10. Drug infusion device 14 is programmable through a telemetry link from programmer 20, which is coupled via a conductor 22 to a radio frequency antenna 24. Drug infusion device 14 could be, but is not limited to being, a pump for infusing fluid medication into a patient's body. Methods of communicating, using radio frequency telemetry, with implanted treatment devices in order to program such implanted drug infusion devices, are well known in the art.

Figure 2:
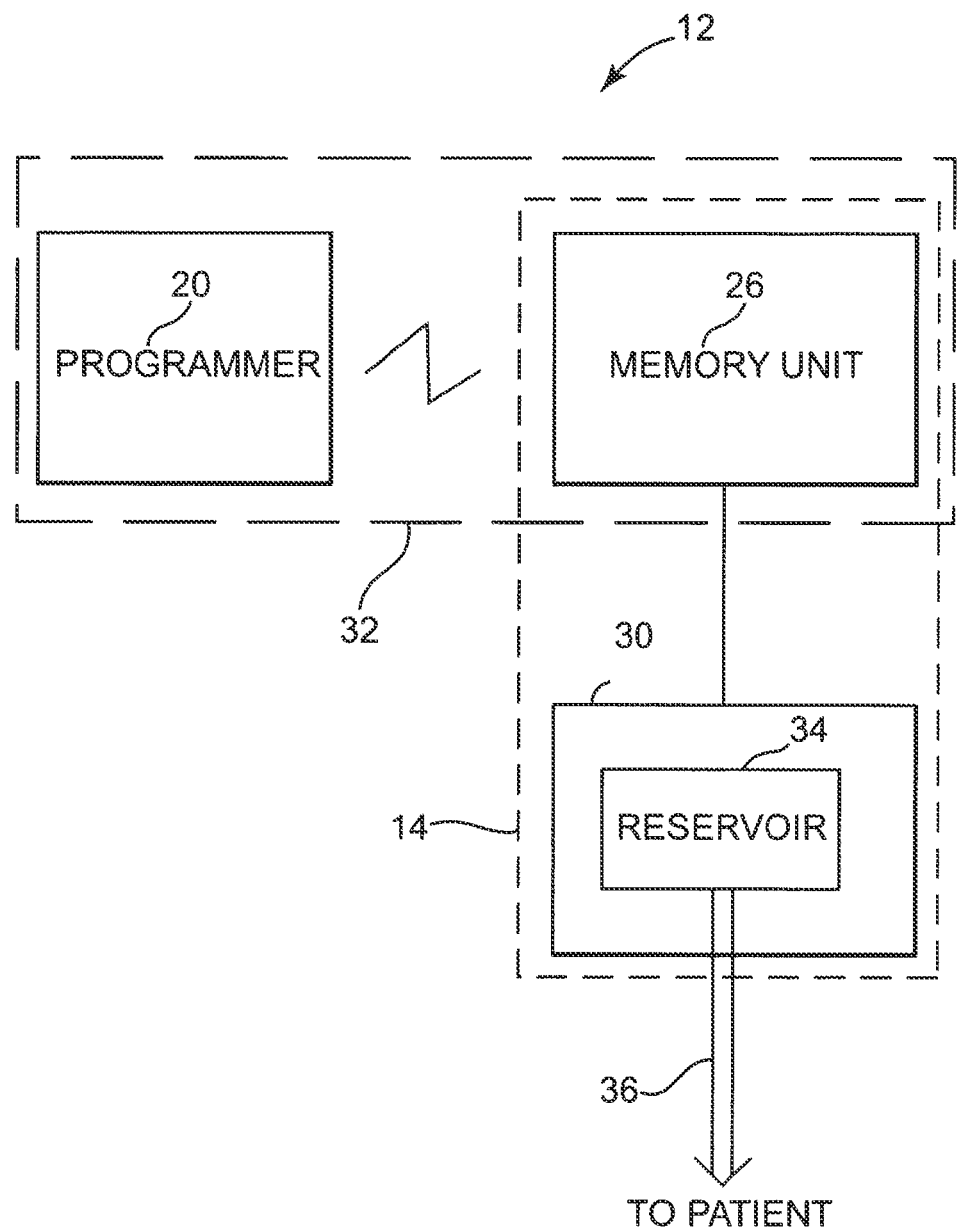
FIG. 2 is a block diagram of a drug infusion system of the present invention having an implantable drug infusion device and an external programmer.

FIG. 2 is a block diagram of drug infusion system 12 having an implantable drug infusion device 14. Drug infusion device 14 consists of an internal memory unit 26 containing memory and registers which provide internal drug delivery instructions to drug delivery module 30. External programmer 20 acts as an input-output device for drug infusion system 12 and also provides computational support for memory unit 26. Memory unit 26 and programmer 20, operating together, function as a controller 32 controlling drug delivery module 30 in the delivery of fluid medication to patient 10. In general, drug delivery module 30 is a pump for infusing a fluid medication, including a drug or a combination of drugs, to patient 10. Drug delivery module 30 has a reservoir 34 for holding the fluid medication to be infused and is coupled to patient 10 through catheter tubing 36. Such drug delivery modules 30 are well known in the art.

Memory 26 receives programming information, via telemetry, from programmer 20 through conventional means. Programming information, once stored in memory unit 26, provides the dosing regimen to be performed by drug delivery module 30.

Drugs may be provided to a patient 10 by drug delivery module 30 at a predetermined dosage, generally calculated as an amount of drug provided to patient 10 in a predetermined period of time. It is typical to specify such dosage as an amount of drug, e.g., measured in milligrams, per day, or per twenty-four hour period. This dosage amount provides the medical professional with information about the probable efficacy of the drug and potential harmful side effects of the drug on patient 10. Typically, enough drug must be administered in order to have a therapeutic effect. At the other end of the scale, the amount of the drug typically must be limited to a maximum amount, typically referred as the maximum daily dose, in order not to avoid potentially damaging side effects.

It is typically relatively easy for a medical professional to determine the proper maximum daily dose for patient 10 that, hopefully, will provide a therapeutic benefit while not producing significant harmful side effects.

However, patient 10 may have a need for differing amounts of a given drug during different time intervals. For example, a patient may have a greater need for a drug which provides therapeutic pain relief during the nighttime hours in order to allow the patient to sleep. Likewise, this same patient may have less of a need for the drug during active daytime hours when the patient is concentrating on other activities. In order to provide the maximum therapeutic effect of the drug during the high-need nighttime hours and to minimize potentially harmful side effects, the drug infusion device may be programmed to deliver a greater amount of the drug during certain time intervals, in this case during the nighttime hours and a lesser amount of the drug during the normally active daytime hours. By cutting down of drug delivery during the active daytime hours, a greater amount of the drug may be delivered by the drug infusion device during the nighttime hours and still keep the maximum daily dose within acceptable limits.

Figure 7:
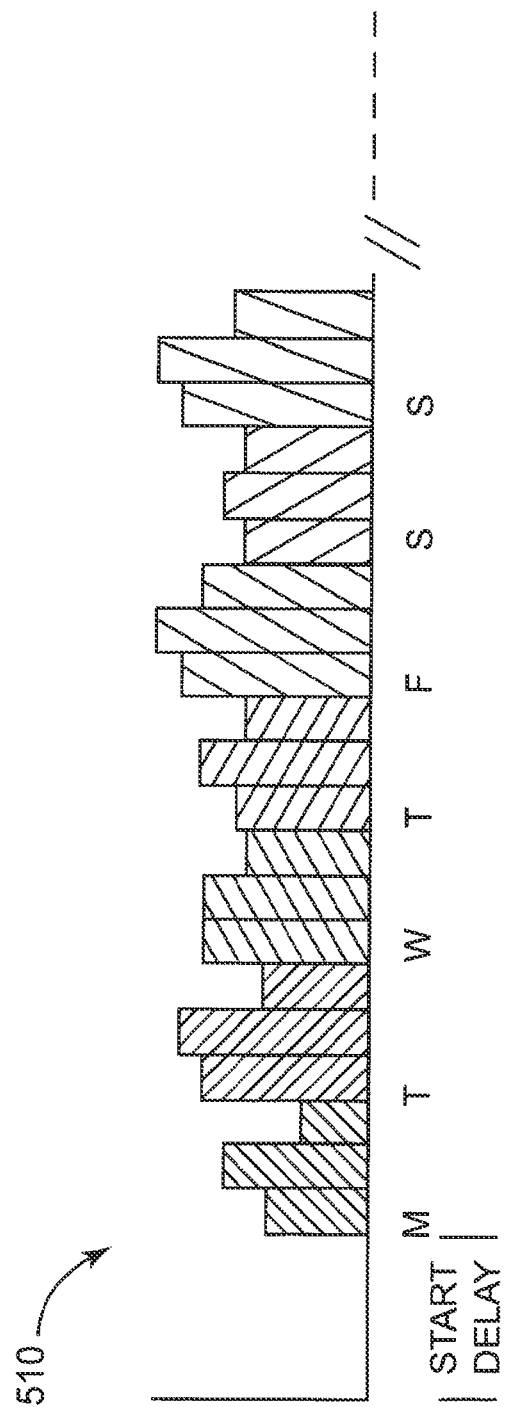
FIG. 7 illustrates a multi-step programming cycle with different delivery rates for different days and different times within each of the days.

In a multi-step or flex prescription table, the dosage of drug or fluid medication delivery changes based on time. The change in drug delivery based on time can have a recurring pattern such as daily or weekly. Examples of multi-step or flex prescription table which have daily recurrence could be different dosage for morning, afternoon, evening and night and for weekly recurrence could be different dosage for different days of the week and/or different dosage for weekday and weekends, etc. The daily and weekly recurrence could be combined such that we have different dosage during the day and during each or a subset of days of the week. Similarly other type of recurrence could also be used with the multi-step/flex prescription table. See, for example, programming cycle 510 in FIG. 7.

Figure 8:
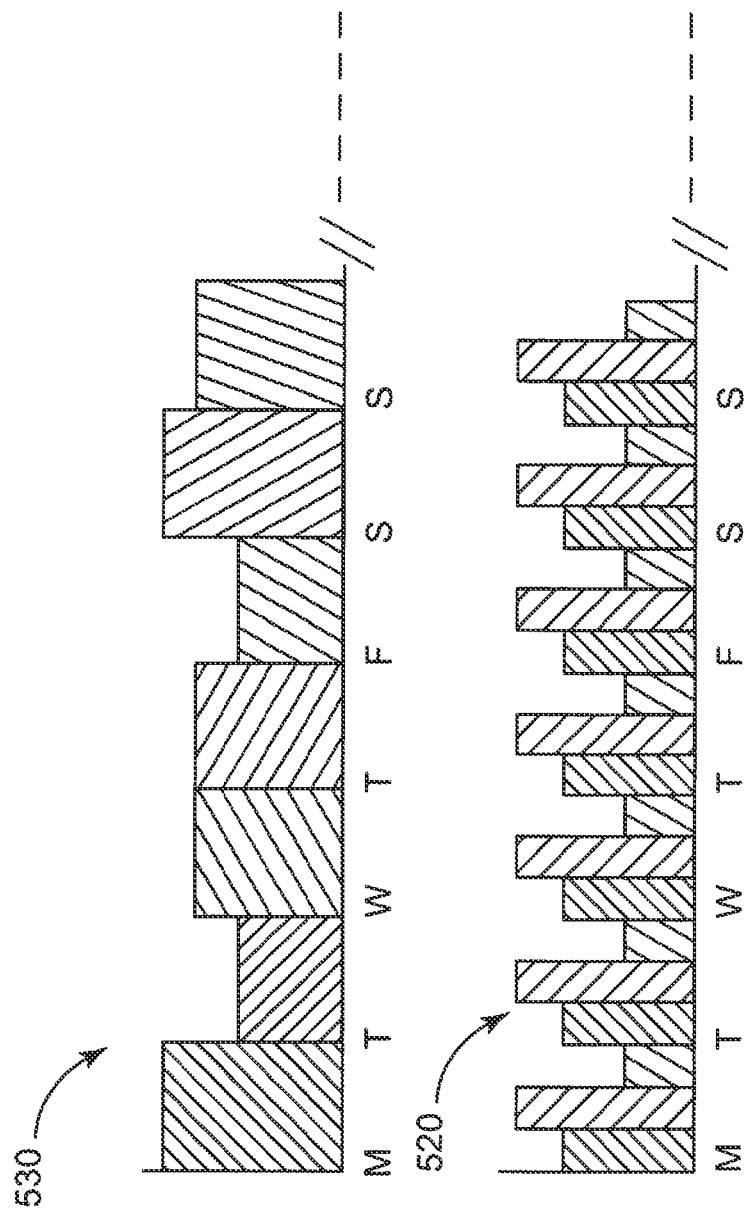
FIG. 8 illustrates a multi-step prescription table with a daily cycle with step changes occurring on an intra day basis (i.e. different parts of the day may have a different dosage) and a multi-step prescription table with a weekly cycle with step changes occurring on a daily basis (i.e. each day of the week may have a different dosage)

The term "cycle" refers to each recurrence of the multi-step/flex prescription table and the term "step" for each transition within a cycle of the prescription table. Note, a prescription may have more than one set of cycles. In cases of multiple cycles, one cycle may be within another cycle (i.e. one cycle is subset of another) or they may be disjointed. An example of a cycle within another cycle is a multi-step/flex prescription table having multiple steps during the day, i.e., during the day cycle, (see, for example programming cycle 520 in FIG. 8) and then different day cycle for each day of the week, i.e., the individual day cycles are considered steps from the weekly cycle's perspective (see, for example programming cycle 530 in FIG. 8). The combined cycle-in-a-cycle programming cycle is illustrated by programming cycle 540 in FIG. 9. An example of a disjointed cycle would be one cycle running for x number of weeks and then another cycle running for the next y number of weeks, etc. See, for example, programming cycles 550 in FIG. 10. Various permutations of the steps and cycles for the prescription table are also contemplated.

Figure 3:
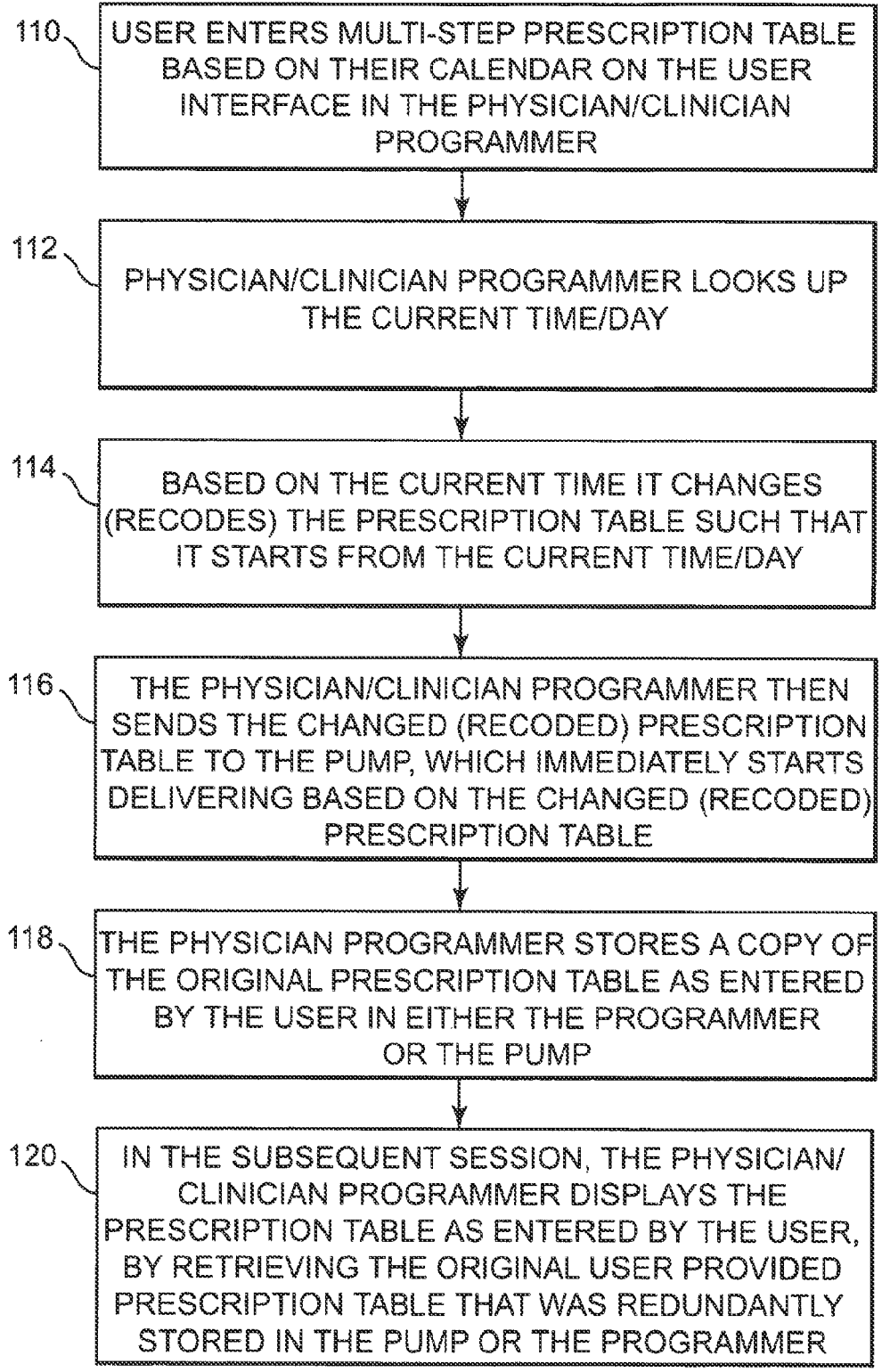
FIG. 3 is a flow chart illustrating an embodiment of the present invention utilizing recoding and redundant storage of prescription tables.

In an embodiment, FIG. 3 illustrates a process of entering a new multi-step prescription table with a daily cycle with step changes occurring on an intra day basis, i.e., different parts of the day may have a different dosage. Since the entering may occur at a time different than the time and/or day on which the prescription table is intended to commence, an accommodation must be made to allow the patient to begin to benefit from the new prescription table without the necessity of waiting for the beginning of the next programming cycle. The user, typically a medical professional, enters (110) the multi-step prescription table, also referred to a program or a programming cycle, based on the calendar, i.e., time frame, on the user-interface in programmer 20. Programmer 20 retrieves (112) the current day and time from memory or, alternatively, the user will enter the current day and time. Based on the current time and current day, programmer 20 changes, i.e., recodes, (114) the prescription table such that the prescription table is viewed as starting from the current time and the current day. With this recoding there is no longer any partial cycles. The delivery cycle starts from the current time/date, instead of the physician/clinician calendar time/date of the programming cycle. Programmer 20 then sends (116) the changed, i.e., recoded, prescription table to the pump, i.e., drug delivery module 30, which immediately starts delivering the fluid medication to the patient based on the changed (recoded) prescription table. Programmer 20 stores (118) a copy of the original prescription table as entered by the user in either programmer 20 or implantable drug infusion device 14. In a subsequent session, programmer 20 may display (120) the prescription table as entered by the user by retrieving the original user provided prescription table that was redundantly stored in programmer 20 or implantable drug infusion device 14.

Figure 4:
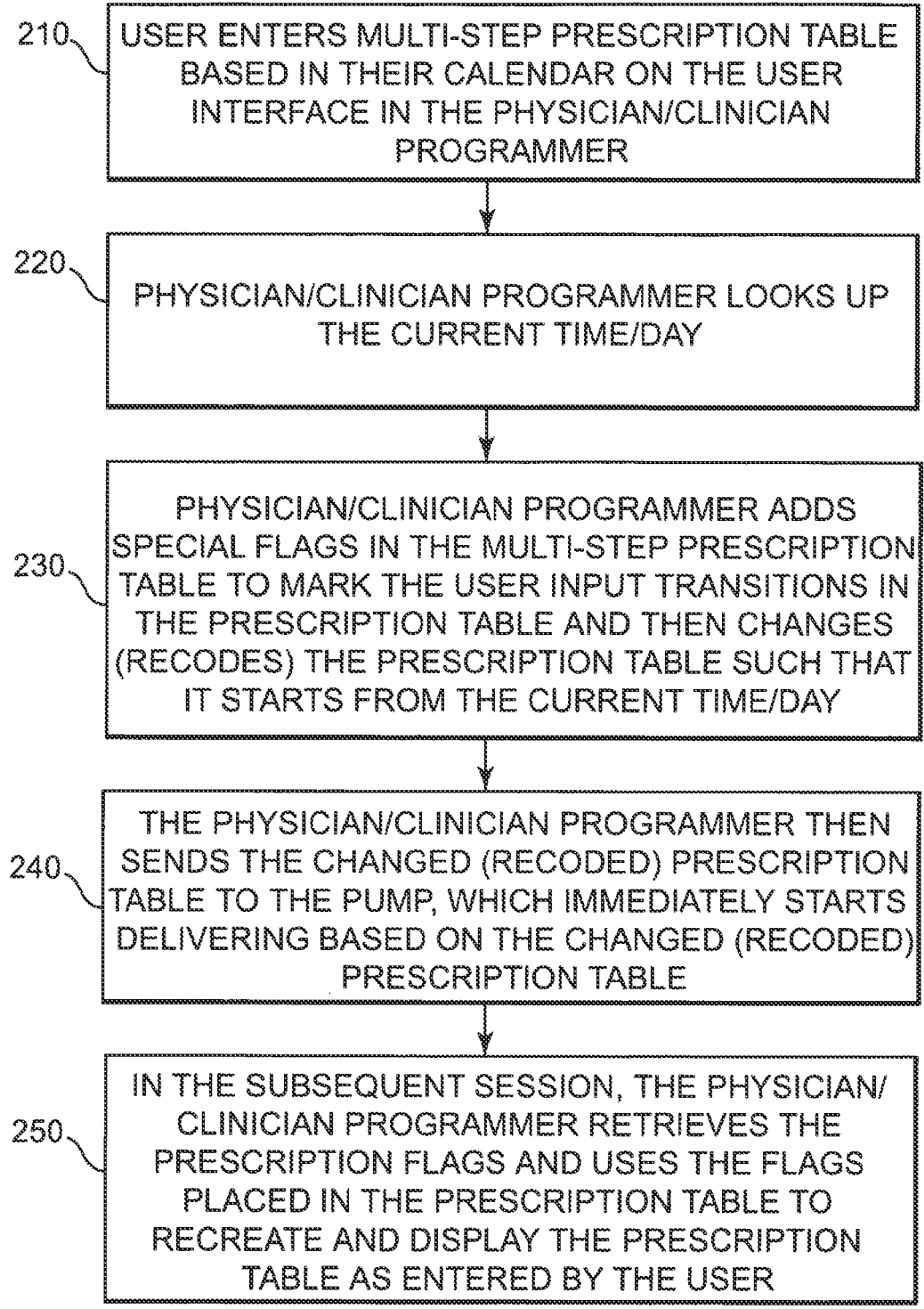
FIG. 4 is a flow chart illustrating an alternative embodiment of the present invention utilizing flags to reconstruct the prescription table.

FIG. 4 illustrates another embodiment of handling the same problem addressed in FIG. 3. The user enters (210) a multi-step prescription table in a conventional manner based on the user's calendar on the user interface in programmer 20. Programmer 20 retrieves (220) the current time and/or day from memory or, alternatively, the user will enter the current time and/or day. Programmer 20 adds (230) special flags in the multi-step prescription table to mark the user input transitions in the prescription table and then changes (recodes) the prescription table such that the prescription table starts from the current time and/or day. These special flags would include a mark for the first step in the cycle as entered by the user and special flags to indicate any breakup of steps within a cycle (i.e. if the prescription is programmed at 6 PM and the step runs from midnight to midnight, then in this scheme we may break it up into two steps) and their recombination points. Programmer 20 then sends (240) the changed (recoded) prescription table to drug infusion device 14 which immediately starts delivering the fluid medication to the patient based on the changed (recoded) prescription table. In a subsequent session, programmer 20 retrieves (250) the specially added prescription flags and uses the flags placed in the prescription table to recreate and display the prescription table as entered by the user. In this method, the prescription table as entered by the physician/clinician based on their calendar does not need to be redundantly stored.

Figure 5:
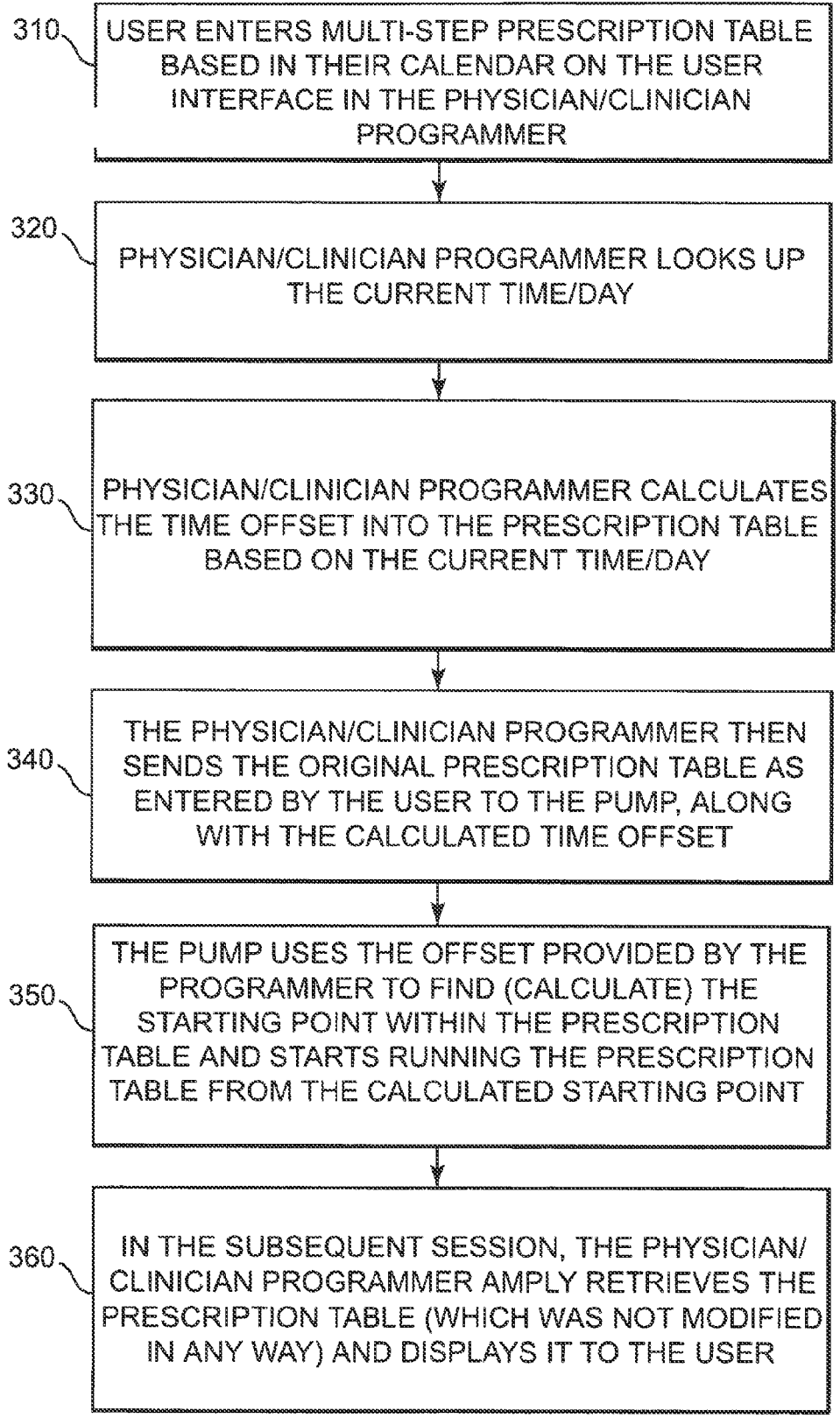
FIG. 5 is a flow chart illustrating an alternative embodiment of the present invention utilizing a calculated offset.

FIG. 5 illustrates still another embodiment of handling the same problem addressed in FIG. 3 with a multi-step prescription table with two cycles which are subset of other. The multi-step prescription table has a daily cycle with intra day step changes and then a weekly cycle in which each day of the week may have a different day cycle. The user enters (310) a multi-step prescription table in a conventional manner based on the user's calendar on the user interface in programmer 20. Programmer 20 retrieves (320) the current time and/or day from memory or, alternatively, the user will enter the current time and/or day. Programmer 20 calculates (330) the time offset between a time associated with the prescription table, e.g., the start time and/or day of the prescription table, and the current time and/or day. Programmer 20 then sends (340) the original prescription table as entered by the user to drug infusion device 14 along with the calculated time offset. Drug infusion device 14 uses (350) the offset provided by programmer 20 to find or calculate the starting point within the prescription table and starts delivering fluid medication to the patient based on the calculated starting point in the prescription table. In a subsequent session, programmer 20 simply retrieves that prescription table which was not modified in any way, from either programmer 20 or drug infusion device 14, and displays the prescription table to the user. With this method there is only one prescription table to store and no recoding of the original prescription table is needed. In addition, no special markers or flags are needed for reconstruction of the prescription table for display during subsequent sessions, i.e. no recoding, reconstruction or redundant storage of prescription table is required.

The method illustrated in FIG. 5 may be the similar to the methods illustrated in FIGS. 3 and 4 (single cycle or multi cycle) with the addition of an intermediary device in between, e.g., a programmer 20 or a remote programming system of some kind. The user creates the multi-step/flex prescription table using the user interface of a physician/clinician programmer 20 and then transmits it to a user programmer 20 or any kind of other programming device using any of the communication mode (some examples would be RE, IR, wireless, blue tooth, phone line, interact etc. etc.) or any combination of the devices and/or communication modes (i.e. RE or IR etc from the physician/clinician programmer 20 to a device that is hooked up to the phone line and then via phone line to a device that is hooked up on the patient side, etc). The patient programmer 20 or the other programming device then downloads the prescription table to drug infusion device 14. The four embodiments illustrated in FIG. 3 through 6 are valid for this implementation. In addition, the recoding and/or calculation of the time offset and/or logic for managing time of day and date may be implemented/present in the intermediary devices and/or patient programmer 20 instead of the physician/clinician programmer 20 or drug infusion device 14.

Figure 6:
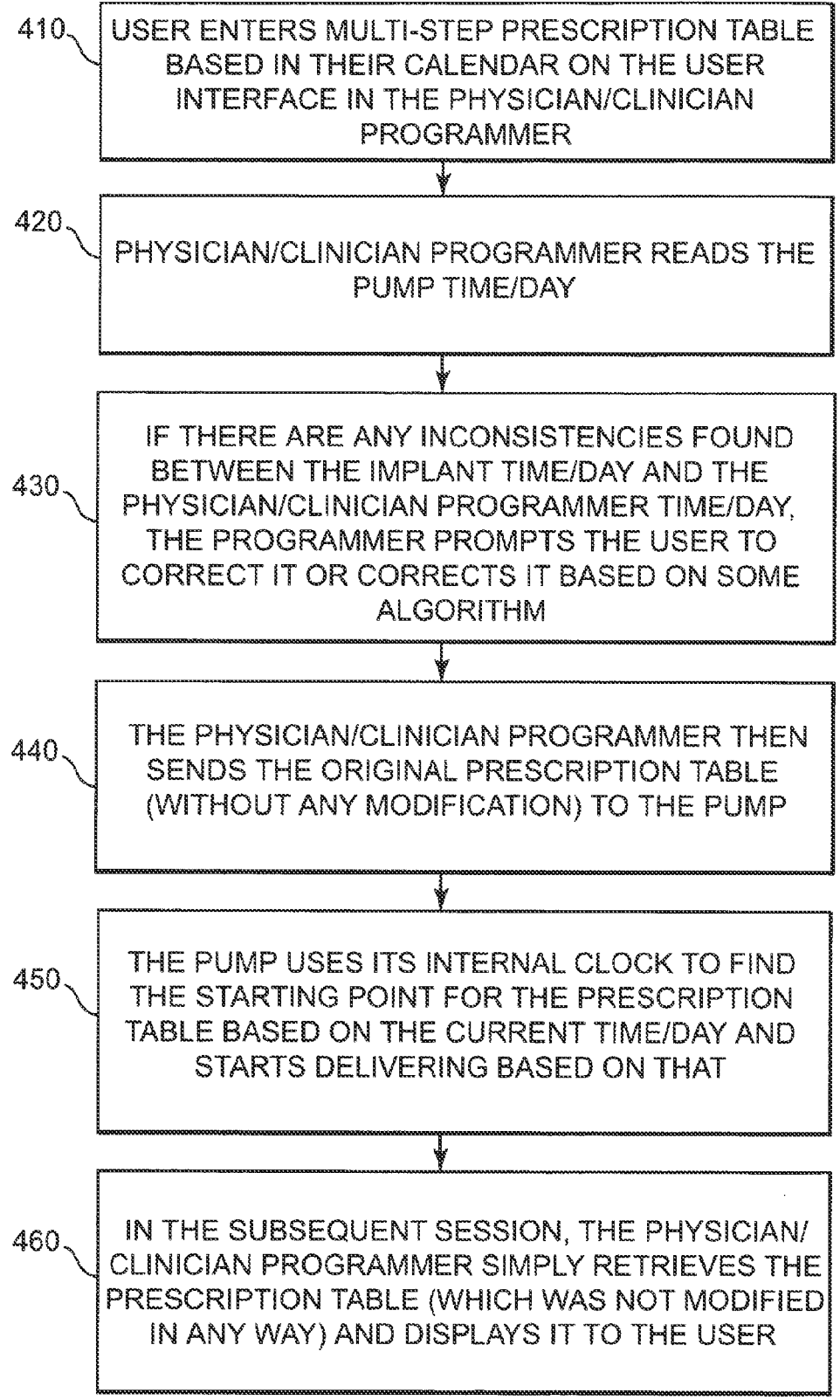
FIG. 6 is a flow chart illustrating an alternative embodiment of the present invention utilizing a start time and/or day kept by the drug infusion device.

FIG. 6 shows, a multi-step prescription table with two disjointed weekly cycles, each with daily steps. The first weekly cycle runs for X weeks and then ends and then the second weekly cycle starts. The time and/or day is stored and/or kept in drug infusion device 14. The user enters (410) a multi-step prescription table in a conventional manner based on the user's calendar on the user interface in programmer 20. Programmer 20 retrieves (420) the current time and/or day from memory or, alternatively, the user will enter the current time and/or day. The user checks to make sure that the implant time of day and date matches its time of day and date. If there are any inconsistencies found between the time and/or day in drug infusion device 14 and current time and/or day in programmer 20, programmer 20 prompts (430) the user to correct the time and/or day or, alternatively, automatically performs the correction. Programmer 20 provides a set of choices/suggestions for the user to follow to resolve them and/or uses some algorithm to resolve the discrepancy. Programmer 20 then sends (440) the original prescription table to drug infusion device 114 without time and/or day starting point modification. If the start of the prescription table is customized by the user based on their preference, then this start of week day/time information of the programming cycle may also be optionally transmitted along with the prescription table to drug infusion device 14. Drug infusion device 14 uses its own internal clock (time and/or day) to find (450) the starting point in the prescription table based on the current time and/or day starts delivering fluid medication based on the current time and/or day. In a subsequent session, programmer 20 retrieves the prescription table, which was not modified, and displays the prescription table to the user. No recoding, reconstruction or redundant storage of the prescription table is required.

The method illustrated in FIG. 6 may be similar to the methods illustrated in FIGS. 3 and 4, or used in combination with the method illustrated in FIG. 5 (e.g., single or multi cycle with only physician/clinician programmer 20 and implantable drug infusion device 14 or any combination of other intermediary devices using any combination of communication modes). All of the illustrated methods provide the physician/clinician with the additional ability to start the prescription table at a programmed delay from the current time. In other words the physician/clinician can program a start delay for the execution of the prescription or program a particular point (time/date) for start of prescription table in the recurring cycle (or in the case of multiple recurring cycle in any one of the cycles). The execution of the prescription table remains pending (after it has been programmed by the physician/clinician) till the time provided by the physician/clinician is reached or the start delay programmed by the physician/clinician expires and then the multi-step prescription table starts execution based on the time/date at that point (and not when the prescription table was programmed by the physician/clinician).

Although multi-step prescription tables are time dependent (the prescription steps and cycles change with time), the physician/clinician would like to view and program the prescription in a time independent calendar manner, either customized to their preference or based on a commonly used standard such as 12:01 a.m. on Monday morning, rather than based on the time when the programming session is taking place.

In the description and illustrations above, a drug infusion system 12 has been described which, preferably, is capable of:

a) Starting from any of the step within the first iteration of the cycle based on the physician/clinician programming calendar and the current time of day and/or current day (i.e. for a prescription that has different dosage for the 7 days of the week, if the programming occurs on Wednesday and the physician/clinician calendar week starts from Monday, then the $1^{st}$ cycle must start from the $3^{rd}$ step);

b) Running the starting step for the first cycle for a shorter duration based on the physician/clinician programming calendar and the current time of the day and/or current day (i.e. for a prescription that has different dosage for the 7 days of the week, if the programming occurs on Wed at 6 PM and the physician/clinician calendar starts at 12:01 AM on Monday, then the prescription must start in the $3^{rd}$ step with only 6 hours left for that step (instead of the usual 24 hrs)).

c) Storing or reconstructing the prescription table such that it can be displayed back to the physician/clinician in the same calendar format during any of the subsequent patient visits as was programmed originally.

d) Displaying to the physician/clinician in any calendar format that the physician/clinician chooses (e.g., the physician/clinician can customize the calendar and the prescription adjusts based on the calendar customization of the physician/clinician) independent of the calendar format used in previous visits. For example, physicians/clinicians in different countries or regions may use calendar formats in their programmer or computer week starting on Monday versus week starting on Saturday).

e) Having a physician/clinician restart a multi-step/flex prescription during subsequent visits using the original multi-step/flex prescription table, with or without changes made to the contents (e.g., dosages) of the prescription table, with the system (rather than physician/clinician) keeping track of the correct time/date to restart the prescription at the appropriate place in the prescription table. The time/day of the subsequent visit will likely be different from the original visit, and it would be undesirable to restart the prescription table at the original starting point. For example, the initial programming of the multi-step prescription table was done at 6 PM on Wednesday, the subsequent visit occurs at 10 AM on Monday, and the prescription has a weekly cycle with daily steps. This capability allows the prescription to be restarted during the subsequent visit at the point on the prescription table corresponding to 10 AM on Monday without the physician/clinician having to pay attention to the time or date.

f) Having a physician/clinician restart a multi-step/flex prescription during subsequent visits using the original multi-step/flex prescription table displayed in a different calendar format, with or without changes made to the contents (e.g., dosages) of the prescription table, with the system (rather than physician/clinician) keeping track of the correct time/date to restart the prescription at the appropriate place in the prescription table. For example, the initial prescription table is created with a calendar format in which the week starts on Monday, and changes are made to the contents of the prescription table during a subsequent visit while using a calendar format in which the week starts on Saturday. The system will restart the prescription at the correct time taking into account the differences of the calendar format without the physician/clinician having to pay attention to the different calendar format.

U.S. patent application Ser. No. 10/278,769, filed Oct. 22, 2002, on "Drug Infusion System Programmable in Flex Mode", now U.S. Pat. No. 7,967,812, issued Jun. 28, 2011, by Keith E. Jasperson, Thomas J. Valine and Frederic J. Wahlquist, and U.S. patent application Ser. No. 10/278,767, filed Oct. 22, 2002, on "Drug Infusion System with Multiple Medications", by Keith E. Jasperson, Thomas J. Valine and Frederic J. Wahlquist, are incorporated herein by reference in their entireties.

While some of the description of the preferred embodiments of the invention have been described as a particular component of drug infusion system 12 performing a particular function, such as calculating an offset time, it is to be recognized and understood that such reference is for convenience only and while such may be the preferred arrangement, the functions performed by various components of drug infusion system 12 could equally well be performed by another component of drug infusion system 12. As an example, certain functions have been ascribed to a programmer 20. It is to be recognized and understood that such functions might as easily be performed by a physician/clinician programmer, by a patient programmer or by another component altogether, such as by implantable drug infusion device 14.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:
1. A drug infusion system for delivering a fluid medication to a patient, comprising:
an implantable drug delivery device configured to deliver said fluid medication at a programmable rate to said patient under control of an original programming cycle having a plurality of steps in a plurality of time slots beginning at a starting time;

said programming cycle specifying said programmable rate for each of said plurality of steps;

an external controller configured to store a program representative of said original programming cycle in said implantable drug delivery device at a programming time, wherein said starting time and said programming time are different; and said drug infusion system adjusting said implantable drug delivery device so that said original programming cycle begins at said programming time at a point during said original programming cycle adjusted for a difference between said starting time and said programming time, wherein said adjusting occurs before said program representative of said original programming cycle is stored in said implantable drug delivery device.

2. A drug infusion system as in claim 1 further comprising an adjusted programming cycle having a new start time corresponding to said programming time and wherein said program representative of said original programming cycle comprises said adjusted programming cycle.

3. A drug infusion system as in claim 2 wherein said original programming cycle is retained.

4. A drug infusion system as in claim 3 wherein said external controller retains said original programming cycle.

5. A drug infusion system as in claim 3 wherein said implantable drug delivery device retains said original programming cycle.

6. A drug infusion system as in claim 2 wherein said original programming cycle is reconstructable from said adjusted programming cycle.

7. A drug infusion system as in claim 6 wherein said adjusted programming cycle contains flags allowing said original programming cycle to be reconstructed from said adjusted programming cycle.

8. A drug infusion system for delivering a fluid medication to a patient, comprising:

an implantable drug delivery device configured to deliver said fluid medication at a programmable rate to said patient under control of an original programming cycle having a plurality of steps in a plurality of time slots beginning at a starting time;

said programming cycle specifying said programmable rate for each of said plurality of steps;

an external controller configured to store a program representative of said original programming cycle in said implantable drug delivery device at a programming time, wherein said starting time and said programming time are different; and said drug infusion system adjusting said implantable drug delivery device so that said original programming cycle begins at said programming time at a point during said original programming cycle adjusted for a difference between said starting time and said programming time, wherein said adjusting occurs after said program representative of said original programming cycle is stored in said implantable drug delivery device and wherein said start time is adjusted using a time obtained from a real time clock internal to said implantable drug delivery device to account for said programming time.

9. A method of programming an implantable drug delivery device adapted to deliver a fluid medication at a programmable rate to a patient in plurality of steps in a plurality of time slots, comprising the steps of:

creating an original programming cycle specifying said programmable rate for each of said plurality of steps on an external controller specifying a starting time for said original programming cycle, wherein said starting time and said programming time are different;

storing a program representative of said original programming cycle in said implantable drug delivery device at a programming time; and adjusting said implantable drug delivery device so that said original programming cycle begins at said programming time at a point during said original programming cycle adjusted for a difference between said starting time and said programming time, wherein said adjusting step occurs before said storing step.

10. A method as in claim 9 wherein said adjusting step comprises the step of creating an adjusted programming cycle having a new start time corresponding to said programming time and wherein said storing step comprises storing said adjusted programming cycle in said implantable drug delivery device.

11. A method as in claim 10 further comprising the step of retaining said original programming cycle.

12. A method as in claim 11 wherein said retaining step retains said original programming cycle external to said implantable drug delivery device.

13. A method as in claim 11 wherein said retaining step retains said original programming cycle in said implantable drug delivery device.

14. A method as in claim 10 wherein said original programming cycle is reconstructable from said adjusted programming cycle.

15. A method as in claim 14 wherein said adjusted programming cycle contains flags allowing said original programming cycle to be reconstructed from said adjusted programming cycle.

16. A method of programming an implantable drug delivery device adapted to deliver a fluid medication at a programmable rate to a patient in plurality of steps in a plurality of time slots, comprising the steps of:

creating an original programming cycle specifying said programmable rate for each of said plurality of steps on an external controller specifying a starting time for said original programming cycle, wherein said starting time and said programming time are different;

storing a program representative of said original programming cycle in said implantable drug delivery device at a programming time; and adjusting said implantable drug delivery device so that said original programming cycle begins at said programming time at a point during said original programming cycle adjusted for a difference between said starting time and said programming time, wherein said adjusting step occurs after said storing step and wherein said adjusting step comprises providing an offset from said start time using a time obtained from a real time clock that is internal to said implantable drug delivery device.

* * * * *